United States Patent [19]

Crocco et al.

[11] Patent Number: 5,646,314

[45] Date of Patent: *Jul. 8, 1997

[54] PROCESS FOR TITANIUM SILICALITE-CATALYZED EPOXIDATION

[75] Inventors: Guy L. Crocco, Wilmington, Del.; John G. Zajacek, Devon, Pa.

[73] Assignee: ARCO Chemical Technology, L.P., Greenville, Del.

[*] Notice: The term of this patent shall not extend beyond the expiration date of Pat. No. 5,374,747.

[21] Appl. No.: 396,319

[22] Filed: Feb. 28, 1995

Related U.S. Application Data

[63] Continuation-in-part of Ser. No. 340,700, Nov. 16, 1994, abandoned.

[51] Int. Cl.$^6$ .................................................. C07C 301/12
[52] U.S. Cl. ........................................................ 549/531
[58] Field of Search ............................................ 549/531

[56] References Cited

U.S. PATENT DOCUMENTS

| | | | |
|---|---|---|---|
| 4,824,976 | 4/1989 | Clerici et al. | 549/531 |
| 4,833,260 | 5/1989 | Neri et al. | 549/531 |
| 4,937,216 | 6/1990 | Clerici et al. | 502/62 |
| 5,214,168 | 5/1993 | Zajacek | 549/531 |
| 5,262,550 | 11/1993 | Crocco et al. | 549/531 |
| 5,354,875 | 10/1994 | Nemeth et al. | 549/531 |
| 5,374,747 | 12/1994 | Saxton et al. | 549/531 |
| 5,384,418 | 1/1995 | Zajacek et al. | 549/531 |
| 5,463,090 | 10/1995 | Rodriguez et al. | 549/531 |
| 5,466,835 | 11/1995 | Nemeth et al. | 549/531 |

FOREIGN PATENT DOCUMENTS 6211821  8/1994  Japan.

OTHER PUBLICATIONS

"Epoxidation of Lower Olefins with Hydrogen Peroxide and Titanium Silicalite" *Journal of Catalysis*, 140, 71–83 (1993), Clerici et al.

*Primary Examiner*—C. Warren Ivy
*Assistant Examiner*—Lyman H. Smith
*Attorney, Agent, or Firm*—Stephen D. Harper

[57] ABSTRACT

The selectivity of an olefin epoxidation process catalyzed by titanium silicalite is improved by performing the epoxidation in the presence of minor amounts of nonbasic salts such as lithium chloride, sodium nitrate, potassium sulfate, and ammonium dihydrogen phosphate. For example, when hydrogen peroxide is reacted with propylene to form propylene oxide, non-selective ring-opening reactions of the propylene oxide are suppressed when low concentrations of a nonbasic salt are added to the hydrogen peroxide feed.

18 Claims, No Drawings

PROCESS FOR TITANIUM SILICALITE-CATALYZED EPOXIDATION

This is a continuation-in-part of application Ser. No. 08/340,700, filed Nov. 16, 1994, now abandoned.

FIELD OF THE INVENTION

This invention relates to methods whereby the efficiency of an olefin epoxidation reaction may be enhanced. In particular, the invention pertains to an epoxidation process wherein a titanium silicalite is utilized in the presence of hydrogen peroxide and a low concentration of a nonbasic salt to selectively catalyze the formation of the epoxide corresponding to the starting olefin.

BACKGROUND OF THE INVENTION

It is well known that the epoxidation of olefinic compounds with hydrogen peroxide may be effectively catalyzed by certain synthetic zeolites containing titanium atoms (see, for example, U.S. Pat. No. 4,833,260). While selectivity to the desired epoxide is generally high, U.S. Pat. No. 4,824,976 proposes that the non-selective ring-opening reactions which take place when epoxidation is performed in a protic medium such as water or alcohol may be suppressed by treating the catalyst prior to the reaction or during the reaction with a suitable acid neutralizing agent. The neutralizing agent is said to neutralize acid groups on the catalyst surface which tend to promote by-product formation. Neutralization, according to the patent, may be accomplished with water soluble basic substances chosen from among strong bases such as NaOH and KOH and weak bases such as $NH_4OH$, $Na_2CO_3$, $NaHCO_3$, $Na_2HPO_4$ and analogous potassium and lithium salts including $K_2CO_3$, $Li_2CO_3$, $KHCO_3$, $LiHCO_3$, and $K_2HPO_4$, alkali and/or alkaline earth salts of carboxylic acids having from 1 to 10 carbon atoms and alkali and/or alkaline earth alcoholates having from 1 to 10 carbon atoms.

SUMMARY OF THE INVENTION

We have now unexpectedly discovered that by carrying out a titanium silicalite-catalyzed epoxidation in the presence of low concentrations of a nonbasic salt, selectivity to epoxide may be significantly improved without detrimental effect on the rate of hydrogen peroxide conversion. This result was surprising in view of the belief in the art, as evidenced by U.S. Pat. No. 4,824,976, that titanium silicalite must be treated with a basic substance or silylated in order to enhance epoxide selectivity. Further, it had previously been reported that the presence of relatively high concentrations of nonbasic salts such as lithium chloride and sodium nitrate during epoxidation decreases the rate at which certain olefins are epoxidized and also adversely affects selectivity to epoxide [(see Clerici et al., *J. Catalysis* 140, 71–83 (1993)]. Thus, the finding that such salts could be used at lower concentrations to actually increase the yield of epoxide obtained using a titanium silicalite catalyst could not have been predicted.

This invention provides a method of epoxidizing an olefin comprising reacting said olefin with hydrogen peroxide in a reaction zone in the presence of a titanium silicalite catalyst and an amount of a nonbasic salt effective to improve selectivity to epoxide.

DETAILED DESCRIPTION OF THE INVENTION

The hydrogen peroxide ($H_2O_2$) utilized as the oxidant in the present invention may be obtained from any suitable source, including, for example, from autoxidation of secondary alcohols using air or other source of molecular oxygen. Suitable secondary alcohols include both aliphatic alcohols such as isopropanol and cyclohexanol as well as aromatic alcohols such as alpha methyl benzyl alcohol and anthrahydroquinones (including alkyl-substituted anthrahydroquinones). The crude reaction product thereby generated may be either used directly in the epoxidation process of this invention or, if so desired, purified, fractionated, concentrated, ion exchanged, or otherwise processed prior to such use. For example, the ketone generated as an autoxidation co-product may be separated, in whole or in part, from the hydrogen peroxide by distillation (where the ketone is relatively volatile) or by extraction with water (where the ketone is substantially immiscible with or insoluble in water). The hydrogen peroxide may alternatively be generated in situ by, for example, combining oxygen, secondary alcohol, olefin, titanium silicalite and nonbasic salt within a reaction zone under conditions effective to accomplish simultaneous secondary alcohol autoxidation and olefin epoxidation. Generally speaking, it will be desirable to employ initial hydrogen peroxide concentrations of from about 1 to 20 weight percent in the liquid phase within the reaction zone.

The ethylenically unsaturated substrate epoxidized in the process of this invention is preferably an organic compound having from two to ten carbon atoms and at least one ethylenically unsaturated functional group (i.e., a carbon-carbon double bond) and may be a cyclic, branched or straight chain aliphatic olefin. More than one carbon-carbon double bond may be present in the olefin; dienes, trienes, and other polyunsaturated substrates thus may be used.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane, and vinyl cyclohexene.

Mixtures of olefins may be epoxidized and resulting mixture of epoxides either employed in mixed form or separated into the different component epoxides.

The process of this invention is especially useful for the epoxidation of $C_2$–$C_{10}$ olefins having the general structure

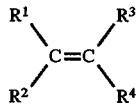

wherein $R^1$, $R^2$, $R^3$, and $R^4$ are the same or different and are selected from the group consisting of hydrogen and $C_1$–$C_8$ alkyl (selected so that the total number of carbons in the olefin does not exceed 10).

The process of this invention is also suitable for use in epoxidizing olefins containing functional groups other than aliphatic hydrocarbyl moieties. For example, the carbon-carbon double bond can be substituted with groups such as —$CO_2H$, —$CO_2R$, —CN, or —OR wherein R is an alkyl, cycloalkyl, aryl or aralkyl substituent. The radicals $R^1$, $R^2$, $R^3$, and $R^4$ in the structural formula shown hereinabove may contain aryl, aralkyl, halo, nitro, sulfonic, cyano, carbonyl (e.g., ketone, aldehyde), hydroxyl, carboxyl (e.g., ester, acid) or ether groups. Examples of olefins of these types include allyl alcohol, styrene, allyl chloride, allyl methyl ether, allyl phenyl ether, methyl methacrylate, acrylic acid, methyl acrylate, stilbene, and the like.

The amount of hydrogen peroxide relative to the amount of olefin is not critical, but most suitably the molar ratio of olefin: hydrogen peroxide is from about 100:1 to 1:10 when the olefin contains one ethylenically unsaturated group. The molar ratio of ethylenically unsaturated groups in the olefin to hydrogen peroxide is more preferably in the range of from 1:2 to 10:1.

The titanium silicalites useful as catalysts in the epoxidation step of the process comprise the class of zeolite substances wherein titanium is substituted for a portion of the silicon atoms in the lattice framework of a molecular sieve. Such substances are well-known in the art.

Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta. The titanium silicalite preferably contains no non-oxygen elements other than titanium and silica in the lattice framework, although minor amounts of boron, iron, aluminum, and the like may be present.

Titanium silicalite catalysts suitable for use in the process of this invention will generally have a composition corresponding to the following empirical formula $xTiO_2$: $(1-x)SiO_2$, where x is between 0.0001 and 0.500. More preferably, the value of x is from 0.01 to 0.125. The molar ratio of Si:Ti in the lattice framework of the titanium silicalite is advantageously from 9.5:1 to 99:1 (most preferably, from 9.5:1 to 60:1). The use of relatively titanium-rich silicalites may also be desirable.

The amount of catalyst employed is not critical, but should be sufficient so as to substantially accomplish the desired epoxidation reaction in a particularly short period of time. The optimum quantity of catalyst will depend upon a number of factors including reaction temperature, olefin reactivity and concentration, hydrogen peroxide concentration, type and concentration of organic solvent as well as catalyst activity and the type of reactor or reaction system (i.e., batch vs. continuous) employed. In a batch-type or slurry reaction, for example, the amount of catalyst will typically be from 0.001 to 10 grams per mole of olefin. In a fixed or packed bed system, the optimum quantity of catalyst will be influenced by the flow rate of reactants through the fixed bed; typically, from about 0.05 to 2.0 kilograms hydrogen peroxide per kilogram catalyst per hour will be utilized. The concentration of titanium in the liquid phase reaction mixture will generally be from about 10 to 10,000 ppm.

The catalyst may be utilized in powder, pellet, microspheric, extruded, monolithic or any other suitable physical form. The use of a binder (co-gel) or support in combination with the titanium silicalite may be advantageous. Supported or bound catalysts may be prepared by the methods known in the art to be effective for zeolite catalysts in general. Preferably, the binder or support is essentially non-acidic and does not catalyze the non-selective decomposition of hydrogen peroxide or ring-opening of the epoxide.

Illustrative binders and supports include titania, silica, alumina, silica-alumina, silicatitania, silica-thoria, silica-magnesia, silica-zironia, silica-beryllia, and ternary compositions of silica with other refractory oxides. Also useful are clays such as montmorillonites, koalins, bentonites, halloysites, dickites, nacrites, and ananxites. The proportion of titanium silicalite:binder or support may range from 99:1 to 1:99, but preferably is from 5:95 to 80:20.

A critical feature of the process of this invention is the presence of a nonbasic salt. While the precise mechanism by which the improved epoxide selectivities of the process are realized is not known, it is believed that the nonbasic salt interacts in a favorable way with the titanium silicalite catalyst so as to suppress undesired side reactions such as epoxide ring-opening. In one embodiment, the titanium silicalite is pretreated (i.e., prior to epoxidation) with the nonbasic salt. One suitable pretreatment method involves forming a slurry of the catalyst in a diluted solution of the nonbasic salt in a suitable solvent for the salt such as water and/or alcohol and stirring the slurry at a temperature of from 20° C. to 100° C. for a time effective to incorporate sufficient nonbasic salt into the pores of the titanium silicalite. The catalyst is thereafter separated from the slurry by suitable means such as filtration, centrifugation, or decantation, washed if so desired, and then, optionally, dried of residual solvent. In another pretreatment method, an as-synthesized titanium silicalite is impregnated with a solution of the nonbasic salt and then calcined. In a preferred embodiment, however, the nonbasic salt is introduced into the reaction zone separately from the catalyst during epoxidation. For example, the nonbasic salt may be suitably dissolved in the hydrogen peroxide feed, which typically will also contain a relatively polar solvent such as water, alcohol, and/or ketone. In a continuous process, the concentration of nonbasic salt in the feed entering the reaction zone may be periodically adjusted as desired or necessary in order to optimize the epoxidation results attained. It may, for example, be advantageous to use a constant salt concentration, to introduce the salt at intermittent intervals, or to increase or decrease the salt concentration over time.

A salt is a compound formed when the proton of an acid is replaced by a metal cation or its equivalent (e.g., $NH_4^+$). Suitable salts for the purpose of this invention include those nonbasic substances which comprise an anion and a cation preferably selected from ammonium ($NH_4$), alkali metals (especially Li, Na, K), and alkaline earth metals. Preferred anions include, but are not limited to, halide (especially Cl and Br), nitrate ($NO_3$), sulfate ($SO_4$), and the anions of phosphorus-, arsenic-, antimony- and tin-containing acids such as phosphate, arsenate, and stannate. Other anions such as formate, acetate, bicarbonate, and the like may, depending upon the identity of the cation, also be used, provided the resulting salt is nonbasic in character. Exemplary nonbasic salts suitable for use include lithium chloride, lithium bromide, sodium chloride, sodium bromide, lithium nitrate, sodium nitrate, potassium nitrate, lithium sulfate, sodium sulfate, potassium sulfate, lithium, magnesium, calcium, barium, and ammonium acetate (and other nonbasic salts of carboxylic acids, especially $C_1$–$C_{10}$ carboxylic acids). Mixtures or combinations of nonbasic salts may be advantageously employed. Preferably, the nonbasic salt is soluble in the liquid phase of the epoxidation reaction mixture (which typically is comprised of hydrogen peroxide, solvent, and olefin). "Nonbasic salt" in the context of this invention means a neutral salt or an acidic salt which when dissolved at a concentration of 0.1N (or to saturation, if the maximum possible concentration is less than 0.1N) in water at 25° C., provides a solution having a pH greater than 4. In one embodiment, an essentially neutral salt is employed.

In one embodiment of this invention, nonbasic salts of phosphorus-, antimony, arsenic-, and tin-containing oxy-acids and hydrous oxides of such elements are utilized. Such oxy-acids and hydrous oxides may be either organic or inorganic in character, including, for example, phosphoric acids, phosphorous acids, phosphonic acids, phosphinic acids, stannic acids, arsenic acids, antimony acids and the like. Specific illustrative examples are ammonium dihydrogen phosphate, sodium dihydrogen phosphate, potassium dihydrogen phosphate, disodium dihydrogen pyrophosphate, and the alkali metal and ammonium salts of (nitrilotris(methylene)) triphosphonic acid, aminotrimethylene phosphonic acid, (1-hydroxyethylidene) diphosphonic acid, and (ethylene dinitrilo)-tetramethylene phosphonic acid and the like as well as the analogous tin, arsenic, and antimony compounds.

An especially desirable embodiment of the present invention involves selecting a nonbasic salt which not only enhances epoxide selectivity when used in combination with a titanium silicalite catalyst but which also acts as a hydrogen peroxide stabilizer during the oxidation of a secondary alcohol to generate the hydrogen peroxide to be used in epoxidation. That is, the nonbasic salt can be introduced during secondary alcohol oxidation and then carried forward in the hydrogen peroxide stream to the olefin epoxidation step. Nonbasic salts of oxy-acids of phosphorus are especially useful for such purpose, particularly those compounds which sequester ions of heavy metals such as ferric, cupric, cobaltic, and chromic ions.

To avoid an undesirable decrease in the rate of hydrogen peroxide conversion, the concentration of nonbasic salt in the liquid phase within the reaction zone should generally be no greater than 0.02M. Below 0.00001M, little or no enhancement in epoxide selectivity is generally observed. The optimum concentration of nonbasic salt which is utilized will vary depending upon a number of factors, including, for example, the chemical identity of the nonbasic salt, temperature, solvent, space velocity, and the like, but may be readily determined by routine experimentation. Generally speaking, the level of nonbasic salt in the liquid phase epoxidation reaction mixture is desirably maintained from about 1 to 1000 ppm.

The epoxidation reaction temperature is preferably from 0° C. to 100° C. (more preferably from 40° C. to 80° C.), which has been found to be sufficient to accomplish selective conversion of the olefin to epoxide within a reasonably short period of time with minimal non-selective decomposition of the hydrogen peroxide. It is generally advantageous to carry out the reaction to achieve as high a hydrogen peroxide conversion as possible, preferably at least 50%, more preferably at least 90%, most preferably at least 99%, consistent with reasonable selectivities. The optimum reaction temperature will be influenced by catalyst concentration and activity, substrate reactivity, reactant concentrations, and type of solvent employed, among other factors. Reaction or residence times of from about 10 minutes to 48 hours will typically be appropriate, depending upon the above-identified variables. The reaction is preferably performed at atmospheric pressure or at elevated pressure (typically, between 1 and 100 atmospheres). Generally, it will be desirable to maintain the reaction components as a liquid mixture. For example, when an olefin such as propylene is used having a boiling point at atmospheric pressure which is less than the epoxidation temperature, a superatmospheric pressure sufficient to maintain the desired concentration of propylene in the liquid phase is preferably utilized.

The epoxidation process of this invention may be carried out in a batch, continuous, or semi-continuous manner using any appropriate type of reaction vessel or apparatus such as a fixed bed, transport bed, stirred slurry, or CSTR reactor. Known methods for conducting metal-catalyzed epoxidations using hydrogen peroxide will generally also be suitable for use. Thus, the reactants may be combined all at once or sequentially. For example, the hydrogen peroxide and/or the olefin may be added incrementally to the reaction zone.

Epoxidation may be performed in the presence of a suitable solvent in order to dissolve or disperse the reactants and to facilitate temperature control. Suitable solvents include, but are not limited to, water, alcohols (especially $C_1$–$C_{10}$ aliphatic alcohols such as methanol and isopropanol), ketones (especially $C_3$–$C_{10}$ ketones such as acetone), and mixtures of such solvents.

Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration (as when a slurry reactor is utilized, for example), the recovered titanium silicalite catalyst may be economically re-used in subsequent epoxidations. Prior to such re-use, the catalyst may, if so desired, be retreated with the nonbasic salt. Where the catalyst is deployed in the form of a fixed bed, the epoxidation product withdrawn as a stream from the epoxidation zone will be essentially catalyst free with the catalyst being retained within the epoxidation zone. Similarly, any unreacted olefin or hydrogen peroxide may be separated and recycled or otherwise disposed of. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment. Regeneration can also include retreatment or reimpregnation with the nonbasic salt.

From the foregoing description, one skilled in the art can readily ascertain the essential characteristics of this invention, and, without departing from the spirit and scope thereof, can make various changes and modifications of the invention to adapt it to various usages, conditions, and embodiments.

EXAMPLES

Comparative Example 1

An isopropanol oxidate that has been fractionated to remove acetone was simulated by combining isopropanol (86 g) with 50% aqueous hydrogen peroxide (14 g). The oxidate was found to contain 6.87 wt % hydrogen peroxide by iodiometric titration. The oxidate (33 g; 0.067 mol $H_2O_2$) and "TS-1" titanium silicalite catalyst (0.37 g) were charged to a 120 ml stainless steel Parr reactor and fitted with a head containing a dip tube attached to a propylene cylinder, a thermocouple, pressure gauge, and pressure relief valve. Propylene (32 mL; 0.39 mol) was added and the reactor thereafter submerged in a preheated oil bath. The reaction mixture was held at 55° C. for 1 hour. The reactor was transferred to an ice bath and vented at 5° C. The reaction product was iodiometrically titrated and analyzed by gas chromatography, yielding the following results:

| | |
|---|---|
| Hydrogen peroxide, % conversion | 94 |
| Selectivity (based on $H_2O_2$), % | |
| Propylene oxide | 74 |
| Acetone | 8 |
| Solvolysis products | 18 |

Example 2

An isopropanol oxidate was simulated by combining isopropanol (43 g), methanol (43 g), and 50% aqueous hydrogen peroxide (14 g); the oxidate contained 6.75 wt % $H_2O_2$. The oxidate (33 g), TS-1 titanium silicalite catalyst (0.37 g), and lithium chloride (0.0029 g) were reacted as described in Comparative Example 1. The following results were obtained:

| | |
|---|---|
| Hydrogen peroxide, % conversion | 99 |
| % Selectivity (based on $H_2O_2$) | |
| Propylene oxide | 93 |
| Acetone | 1 |
| Solvolysis products | 6 |

Comparative Example 3

Example 2 was repeated using lithium acetate dihydrate (0.0025 g) instead of lithium chloride. The following results were obtained:

| | |
|---|---|
| Hydrogen peroxide, % conversion | 99 |
| % Selectivity (based on $H_2O_2$) | |
| Propylene oxide | 91 |
| Acetone | 2 |
| Solvolysis products | 7 |

Examples 2 and 3 demonstrate that a nonbasic salt such as lithium chloride is, contrary to expectation, as effective as lithium acetate (one of the basic substances suggested by U.S. Pat. No. 4,824,976) in improving the selectivity of a titanium silicalite epoxidation catalyst.

Examples 4–6

Additional epoxidation runs were performed as described in Example 2 using 0.37 g TS-1 titanium silicalite catalyst and different nonbasic salts. The concentration listed is the concentration of nonbasic salt in the oxidate.

| Example No. | 4 | 5 | 6 |
|---|---|---|---|
| Nonbasic salt (ppm) | $Na_2SO_4$(114) | $LiNO_3$(106) | NaCl(87) |
| Hydrogen peroxide, % conversion | 99 | 96 | 99 |
| Selectivity (based on $H_2O_2$), % | | | |
| Propylene oxide | 89 | 90 | 87 |
| Acetone | 1 | 1 | 2 |
| Solvolysis products | 10 | 9 | 11 |

The above results show that a variety of alkali metal salts containing nonbasic anions can be used at low concentrations to enhance selectivity to epoxide.

Comparative Examples 7–9

Examples 4–6 were repeated using certain of the basic substances described in U.S. Pat. No. 4,824,976 instead of the nonbasic salts employed in the process of this invention. In general, selectivity to propylene oxide was approximately the same no matter which additive was employed.

| Example No. | 7 | 8 | 9 |
|---|---|---|---|
| Basic substance (ppm) | $Na_2HPO_4$(61) | NaOAc(36) | NaOH(740) |
| Hydrogen peroxide, % conversion | 92 | 96 | 97 |
| Selectivity (based on $H_2O_2$), % | | | |
| Propylene oxide | 90 | 90 | 89 |
| Acetone | 3 | 2 | 3 |
| Solvolysis products | 7 | 8 | 8 |

Examples 10–11

Examples 4–6 were repeated using magnesium acetate and ammonium acetate as the nonbasic salt. Despite the fact that these salts are essentially neutral or slightly acidic, in contrast to the basic sodium acetate used in Comparative Example 8, comparable epoxidation results were obtained. This result was unexpected in light of the teaching of U.S. Patent No. 4,824,976 that basic substances are needed to improve epoxide selectivity.

| Example No. | 10 | 11 |
|---|---|---|
| Nonbasic salt (ppm) | $Mg(OAc)_2$(213) | $NH_4OAc$(82) |
| Hydrogen peroxide, % conversion | 96 | 96 |
| Selectivity (based on $H_2O_2$), % | | |
| Propylene oxide | 87 | 91 |
| Acetone | 2 | 2 |
| Solvolysis products | 11 | 7 |

Comparative Example 12

An isopropanol oxidate that has been fractionated to remove acetone and diluted with methanol was simulated by combining isopropanol (43 g), methanol (43 g), 50% aqueous $H_2O_2$ (14 g), acetic acid (0.60 g) and formic acid (0.15). The oxidate contained 6.88 wt. % $H_2O_2$ by iodometric titration. The oxidate (33g; 0.065 mol $H_2O_2$) and TS-1 titanium silicalite catalyst (0.37 g) were reacted as described in Comparative Example 1, with the following results:

| Hydrogen Peroxide, % conversion | 99 |
|---|---|
| Selectivity (based on H$_2$O$_2$), % | |
| Propylene Oxide | 79 |
| Acetone | 2 |
| Solvolysis Products | 19 |

Example 13

Comparative Example 12 was repeated, but with lithium nitrate (0.0038g; 114 ppm) added to the oxidate:

| Hydrogen Peroxide, % conversion | 99 |
|---|---|
| Selectivity (based on H$_2$O$_2$), % | |
| Propylene Oxide | 88 |
| Acetone | 2 |
| Solvolysis Products | 10 |

The addition of the nonbasic salt resulted in a 9 point increase in epoxide selectivity, but no loss of catalyst activity, as compared to Comparative Example 11.

Examples 14–20

A series of batch propylene epoxidations was performed using ammonium or sodium dihydrogen phosphate as the nonbasic salt. The liquid feed (33 g) to the reactor contained 82% isopropanol, 15% water, 3% hydrogen peroxide, 0.2% acetic acid, and 0.025% formic acid. The catalyst used was TS-1 titanium silicalite in powder form (0.20 g). The results obtained, shown in Table I, confirm that selectivity to propylene oxide is significantly improved when nonbasic salt is present as compared to the control run (Example 14) with no salt added. Surprisingly, the amount of ring-opened by-products formed is reduced despite the fact that the phosphate salts are somewhat acidic in character. Normally, ring-opening of an epoxide is promoted by the presence of acidic substances.

provide a solution having pH greater than 4, said nonbasic salt being present at a concentration of from 0.00001M to 0.02M in said liquid phase.

2. The method of claim 1 wherein the nonbasic salt is selected from the group consisting of ammonium, alkali metal, and alkaline earth halides, ammonium, alkali metal, and alkaline earth nitrates, ammonium, alkali metal, and alkaline earth sulfates, ammonium, lithium, barium, calcium and magnesium salts of C$_1$–C$_{10}$ carboxylic acids, and ammonium, alkali metal, and alkaline earth salts of phosphorus-containing oxy-acids.

3. The method of claim 1 wherein said reacting is performed at a temperature of from 0° C. to 100° C.

4. The method of claim 1 wherein the liquid phase is comprised of a solvent selected from the group consisting of water, C$_1$–C$_{10}$ alcohols, C$_3$–C$_{10}$ ketones, and mixtures thereof.

5. The method of claim 1 wherein the titanium silicalite catalyst has an MFI, MEL, or zeolite beta topology.

6. The method of claim 1 wherein the olefin is a C$_2$–C$_{10}$ aliphatic olefin.

7. The method of claim 1 wherein the titanium silicalite catalyst has a composition corresponding to the chemical formula xTiO$_2$:(1-x)SiO$_2$ wherein x is from 0.01 to 0.125.

8. The method of claim 1 wherein said reacting is carried out continuously.

9. The method of claim 1 wherein the titanium silicalite catalyst is deployed in the reaction zone in the form of a fixed bed.

10. The method of claim 1 wherein the titanium silicalite catalyst is deployed in the reaction zone in the form of a slurry.

11. A method for epoxidizing a C$_2$–C$_{10}$ aliphatic olefin comprising reacting said C$_2$–C$_{10}$ aliphatic olefin with hydrogen peroxide in a liquid phase within a reaction zone with a nonbasic salt selected from the group consisting of neutral salts and acidic salts which when dissolved at a concentration of 0.1N, or to saturation if the maximum possible concentration is less than 0.1N, in water at 25° C. provide a

TABLE I

| Example | 14 | 15 | 16 | 17 | 18 | 19 | 20 |
|---|---|---|---|---|---|---|---|
| Nonbasic Salt | none | (NH$_4$)H$_2$PO$_4$ | (NH$_4$)H$_2$PO$_4$ | (NH$_4$)H$_2$PO$_4$ | NaH$_2$PO$_4$ | NaH$_2$PO$_4$ | NaH$_2$PO$_4$ |
| (ppm) | — | 26 | 61 | 61 | 62 | 120 | 66 |
| Temp., °C. | 60 | 60 | 60 | 60 | 58 | 58 | 66 |
| H$_2$O$_2$ Conversion, % | 85 | 85 | 95 | 91 | 83 | 87 | 94 |
| Selectivities, % | | | | | | | |
| Propylene Oxide | 83 | 90 | 91 | 93 | 91 | 90 | 92 |
| Acetone | 4.5 | 5.0 | 4.5 | 4.4 | 4.9 | 5.1 | 4.8 |
| Propylene Glycol | 4.5 | 1.4 | 0.7 | 0.7 | 0.7 | 0.5 | 0.9 |
| Propylene Glycol Isopropyl Ether | 2.6 | 1.0 | 0.6 | 0.6 | 0.8 | 0.6 | 1.3 |
| Oxygen | 0 | 0.4 | 0.7 | 0.6 | 0.8 | 0.8 | 0.5 |

We claim:

1. A method for expoxidizing an olefin comprising reacting said olefin with hydrogen peroxide in a liquid phase within a reaction zone in the presence of a titanium silicalite catalyst and a nonbasic salt selected from the group consisting of neutral salts and acidic salts which when dissolved at a concentration of 0.1N, or to saturation if the maximum possible concentration is less than 0.1N, in water at 25° C. provide a solution having a pH of greater than 4, wherein said nonbasic salt is comprised of a cation selected from the group consisting of NH$_4$, Li, Na, K, Mg, and Ca and an anion selected from the group consisting of Cl, Br, NO$_3$, SO$_4$, phosphate, and acetate, subject to the proviso that when the anion is acetate, the cation is a cation other than Na and K, said nonbasic salt being present at a concentration of from 0.00001M to 0.02M in said liquid phase.

12. The method of claim 11 wherein the nonbasic salt is selected from the group consisting of lithium chloride, sodium sulfate, lithium nitrate, magnesium acetate, ammonium acetate, ammonium dihydrogen phosphate, and sodium dihydrogen phosphate.

13. The method of claim 11 wherein the $C_2$–$C_{10}$ aliphatic olefin is propylene.

14. The method of claim 11 wherein the titanium silicalite catalyst is deployed in the form of a fixed bed within the reaction zone.

15. The method of claim 14 wherein the $C_2$–$C_{10}$ aliphatic olefin, hydrogen peroxide, solvent, and nonbasic salt are introduced into the reaction zone and a product stream comprised of an epoxide corresponding to the $C_2$–$C_{10}$ aliphatic olefin is withdrawn from the reaction zone.

16. The method of claim 11 wherein the solvent is selected from the group consisting of water, $C_1$–$C_{10}$ alcohols, $C_3$–$C_{10}$ ketones and mixtures thereof.

17. The method of claim 11 wherein the temperature is from 40° C. to 80° C.

18. The method of claim 13 wherein the titanium silicalite has an MFI topology and a composition corresponding to the chemical formula $xTiO_2:(1-x) SiO_2$, wherein x is from 0.01 to 0.125.

* * * * *